United States Patent [19]

St. Pierre

[11] Patent Number: 4,896,679
[45] Date of Patent: Jan. 30, 1990

[54] METHOD AND APPARATUS FOR THE EXCLUSION OF SOUND AND WATER FROM THE AUDITORY CANAL

[76] Inventor: Carol L. St. Pierre, 3325 E. Jasper St., Tulsa, Okla. 74115

[21] Appl. No.: 355,640

[22] Filed: May 22, 1989

[51] Int. Cl.$^4$ .............................................. A61F 11/00
[52] U.S. Cl. .................................... 128/865; 128/864; 128/868
[58] Field of Search ............... 128/864, 865, 866, 867, 128/868, 264

[56] References Cited

U.S. PATENT DOCUMENTS

| | | | |
|---|---|---|---|
| 1,016,877 | 2/1912 | Elliott | 128/867 |
| 2,719,523 | 10/1955 | Von Gierke | 128/664 |
| 2,876,767 | 3/1959 | Wasserman | 128/865 |
| 3,110,356 | 11/1963 | Mendelson | 181/130 |
| 3,415,246 | 12/1968 | Hill | 128/864 |
| 3,505,999 | 4/1970 | Harvey et al. | 128/865 |
| 3,602,654 | 8/1971 | Victoreen | 181/130 |
| 3,783,864 | 1/1974 | Moller | 128/864 |
| 3,800,791 | 4/1974 | Visor | 128/864 |
| 3,811,437 | 5/1974 | Gardner, Jr. | 128/864 |
| 3,881,570 | 5/1975 | Lewis | 181/135 |
| 4,006,796 | 2/1977 | Coehorst | 181/130 |
| 4,089,332 | 5/1978 | Rose | 128/865 |
| 4,134,153 | 1/1979 | Voorhees | 2/174 |
| 4,193,396 | 3/1980 | Wacker | 128/864 |
| 4,253,452 | 3/1981 | Powers et al. | 128/864 |
| 4,314,553 | 2/1982 | Westerdal | 128/864 |
| 4,384,575 | 5/1983 | Asker | 128/865 |
| 4,406,282 | 9/1983 | Parker et al. | 128/865 |
| 4,724,922 | 2/1988 | Kalayjian | 181/135 |
| 4,774,938 | 10/1988 | Leight | 128/864 |

*Primary Examiner*—Mickey Yu
*Assistant Examiner*—Lynda M. Cofsky

[57] ABSTRACT

A method and apparatus for providing improved protection for the auditory systems of persons who may be subjected to excessive sound pressures or concussive shock waves or who may have certain disorders of the ear which require the exclusion of foreign matter or fluids from the auditory canal, comprising an earplug or an earplug set in which auditory canal inserts may be pneumatically expanded into positive sealing engagement with the auditory meatus by the application of orally-blown pneumatic pressure developed by the human pulmonary system.

9 Claims, 2 Drawing Sheets

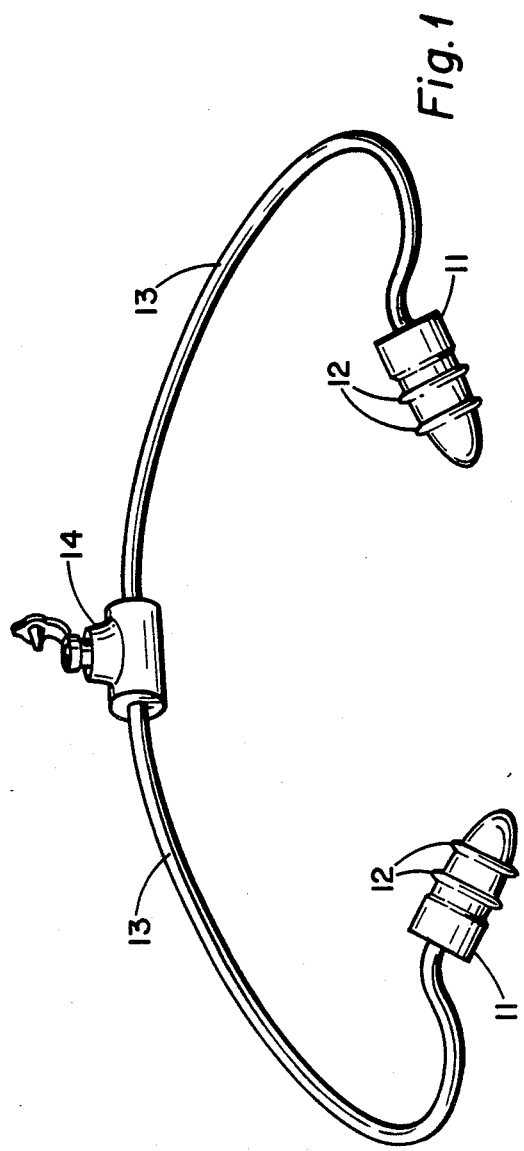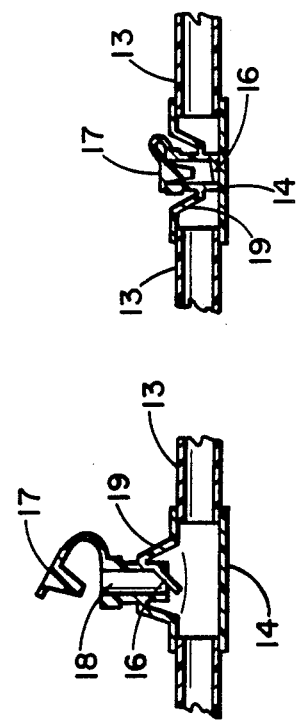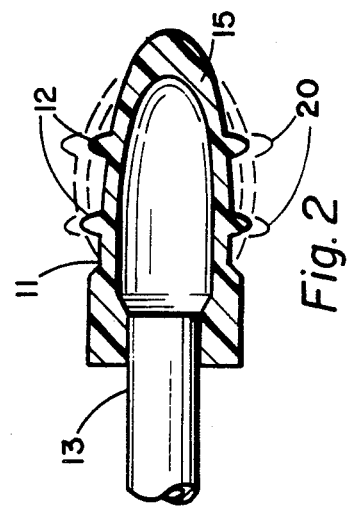

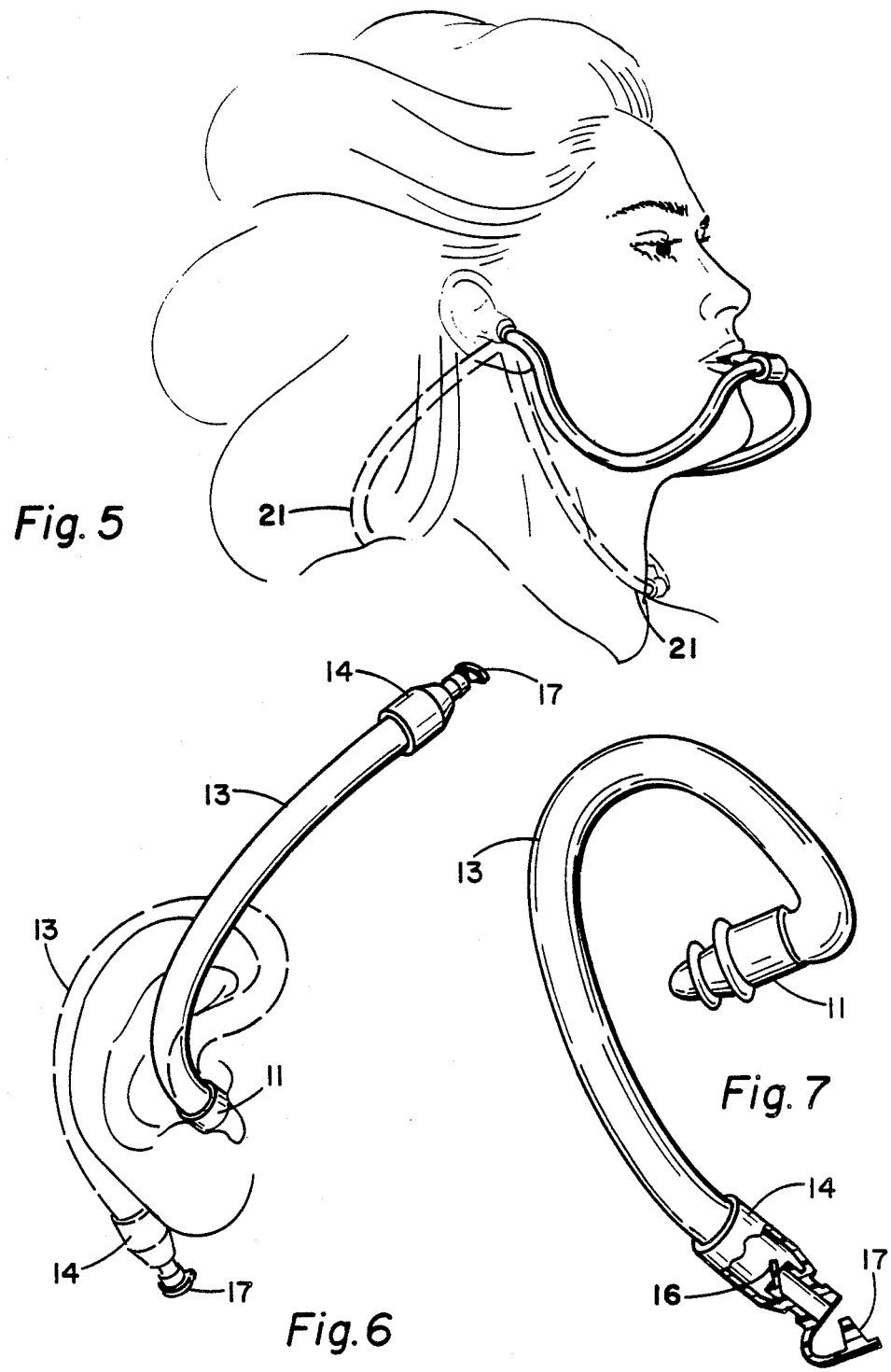

METHOD AND APPARATUS FOR THE EXCLUSION OF SOUND AND WATER FROM THE AUDITORY CANAL

BACKGROUND OF THE INVENTION

It is well known that the human ear is subject to serious damage by exposure to excessive sound or concussive pressures. It is also well known that the entry of water into normally healthy ears often precipitates the onset of ear infections which may result in potentially serious complications. Persons who suffer from chronic middle-ear disease with perforation of the tympanic membrane, Otitis Externa or Media, Otomycosis or Otorreah must constantly guard against the introduction of water to the auditory canal or face serious consequences. These persons cannot safely shower, shampoo, bathe, swim or even be caught in the rain without risking the dangerous possibility that water may enter the ear. To prevent irreversible damage, persons subject to these conditions must utilize means to effectively exclude sound and/or water from the auditory canal.

Many devices and appliances have been developed to provide protection to individuals who must endure high noise levels or who suffer from disorders of the auditory system. As early as 1912 efforts were being made to attenuate sound and lessen the effects of concussive pressures to prevent damage to the ear.

In U.S. Pat. No. 1,016,877 Elliott disclosed an earplug which is strikingly similar to many in current usage. Von Gierke in U.S. Pat. No. 2,719,523 discloses a sound attenuating earplug which provides either positive or negative pressure within the auditory canal to cause a flexure of the tympanic membrane to reduce it's sensitivity to certain frequencies of the sound spectrum.

Expansive earplugs, in many forms, are disclosed in the prior art; by Wasserman in U.S. Pat. No. 2,876,767 wherein a balloon-like earplug is inflated by an externally attachable bulb or syringe; by Mendelson in U.S. Pat. No. 3,110,355 wherein a liquid is injected into a peripheral expansive chamber about a sound transmitting tube to cause said chamber to expand into positive contact with the auditory meatus; by Harvey in U.S. Pat. No. 3,505,999 who utilizes an expandable bag which is pressurized by a syringe-like pump and by Victoreen in U.S. Pat. No. 3,602,654 wherein hydraulic pressure is again utilized to expand a fluid-expandable means into close fitting engagement with the wall of the auditory canal.

In U.S. Pat. No. 3,783,864 Moller discloses an earplug which is expanded by the application of mechanical compression along the longitudinal axis of the insert to cause sealing engagement with the auditory meatus. In U.S. Pat. No. 3,800,791 Visor teaches a method whereby a flexible earplug is expanded by forcing a piston-like expander into the core of the earplug thereby creating an earplug which fits all sizes of auditory canals and Coehorst in U.S. Pat. No. 4,006,796 discloses an earpiece which substantially consists of a thin-walled flexible capsule filled with a jelly-like compound and means to compress said compound into said capsule to cause it to expand into engagement with the inner wall of the ear.

Plastic memory is utilized by Gardner, Jr. in U.S. Pat. No. 3,811,437, by Lewis in U.S. Pat. No. 3,881,570, by Kalayjian in U.S. Pat. No. 4,724,922 to cause earplugs to expand after compression and insertion into the ear canal.

A pneumatic shaping earplug is disclosed by Rose in U.S. Pat. No. 4,089,332 wherein a diaphragmatic member, upon depression, causes a reduction in the volume of the earplug which reacts to said reduction by expanding peripherally in response to the increased pneumatic pressure within said reduced volume.

Earplugs which are connected by flexible means for prevention of loss or for acoustic purposes are disclosed in U.S. Pat. Nos. by; Hill in 3,415,246; Wacker in 4,193,369; Powers et al in 4,253,425; and Westerdahl in 4,314,553.

In U.S. Pat. No. 4,134,153 Voorhees discloses an ear protector which is worn externally of the auditory canal, having pressure-sensitive adhesive means for securing said ear protector to the skin surrounding the base of the ear, further emphasizing the requirement for preventing the entrance of foreign matter or fluid into the auditory canal.

Other recent developments in ear protection technology are disclosed in U.S. Pat. Nos. by; Asker in 4,384,575; Parker et al. in 4,406,282; and Leight in 4,774,938. While these disclosures have no relevance to the present invention, they are herein cited to illustrate the long-standing and continuing effort to provide maximum protection to the delicate elements of the auditory system.

While all the examples of the prior art provide some measure of benefit or protection for the user, concern exists that the use of pneumatically or hydraulically expanded earplugs may possibly represent a hazard potential to the user greater than the benefits or protection to be derived from their use.

Laboratory testing confirms that pneumatic pressures in excess of 300 mm.Hg. are easily developed through the use of a bulb-type syringe. Pressure of this magnitude could possibly cause the rupture of the thin membrane of the earplug, resulting in catastrophic damage to the delicate auditory system. Further, as the pneumatically expanded earplugs come into engagement with the inner circumference of the auditory canal, peripheral expansion ceases and longitudinal expansion begins, making it possible for said earplug to elongate into contact with the tympanic membrane thereby causing possible permanent damage to this delicate tissue.

Pressures achievable through the use of a piston-type syringe acting upon a hydraulic media are of an even greater magnitude and due to the incompressible nature of said hydraulic media, the reaction to movement of the piston is instantaneous, creating an even greater potential for tragic result. This hazard is further compounded when these devices are employed by persons who are untrained in their use.

One other problem associated with the use of pressure-expandable earplugs which employ an externally attachable or detachable pressurizing means is the requirement that the user is subject to the inconvenience of having to carry said pressurizing means in order to be able to utilize said earplugs.

Tests, conducted on a plurality of individuals, have shown the average pressure achievable by the human pulmonary system, when mouth-blown into a flexible plastic tube of an outside diameter of 7.65 mm., to be 93.33 mm.Hg., while the maximum pressure achieved by any individual was 128 mm.Hg. While the pulmonary system may posess the capability of producing greater pressure, the musculature of the lips was incapable of preventing leakage around said small diameter tube.

It is concluded that mouth-blown pressures are self-limiting and as a consequence would be incapable of causing the rupture or over-elongation of well designed inflatable earplugs.

It is the object of the present invention to provide pneumatically inflatable earplugs comprising means whereby the user causes the expansion of said earplugs through the application of self-developed pulmonary pressure. It is a further object of this invention to provide inflatable earplugs which may be safely expanded by an untrained user, to bring said earplugs into positive sealing engagement with the auditory meatus to prevent the entry of damaging sound pressures, concussive shock-waves, foreign matter or fluids into the auditory canal. It is yet a further object of the present invention to provide expandable earplugs for use by infants, the infirm or the handicapped, which may be safely inflated by a care-giver, to provide the aforesaid benefits and protection to these individuals.

SUMMARY OF THE INVENTION

The present invention is a method and apparatus for providing pneumatically expandable earplugs which are inflatable into positive sealing engagement with the auditory meatus to prevent the entry of sound pressures, concussive shock-waves, foreign matter or fluids into the auditory canal comprising means whereby said earplugs are safely inflatable by and through the application of user-developed pulmonary pressure. Said earplugs comprising a connecting flexible tube having proximate the mid-point thereof valve means capable of retaining inflation pressure, and providing means for releasing said pressure to allow the removal of said inflatable earplugs. In an alternate embodiment of the present invention, individual earplugs, each having separate means for inflation and deflation would be provided as will be shown in the drawings.

DESCRIPTION OF THE FIGURES OF THE DRAWINGS

FIG. 1 is an overall view of the device configured for use in both ears, showing the earplugs, the inter-connecting flexible tubing and the valve assembly in the open position, ready for use to inflate the earplugs.

FIG. 2 is a cutaway view of an earplug, typical to both ears, depicting the earplug in the deflated condition (by solid lines) and in the inflated condition (by phantom lines).

FIG. 3 is a cutaway view of the valve device depicting the valve in the position for inflation and showing the "check" or pressure retaining feature of the valve.

FIG. 4 is a cutaway view of the valve device depicting the valve in the closed and retracted position following inflation of the earplugs.

FIG. 5 illustrates the inflatiion procedure (by solid lines) and the placement of the inflating tube following inflation and during use (by phantom lines).

FIG. 6 depicts an alternate embodiment of the invention wherein a separate inflatable earplug may be used for each ear (by solid lines) and the manner in which the inflating tube may be placed behind the ear (by phantom lines) following inflation and during use.

FIG. 7 is an overall illustration of the alternate embodiment of the inflatable earplug device in the deflated condition showing the valve device and pressure retaining feature of the valve in cutaway section.

DETAILED DESCRIPTION OF THE DRAWING FIGURES

The embodiment of the present invention is depicted in FIG. 1 of the drawings wherein identical bullet-shaped inflatable earplugs 11, formed of a soft, elastic material having a plurality of integral annuli 12 about their periphery are inter-connected by a flexible plastic tube 13, having proximate the mid-point thereof valve means 14 for receiving and retaining pressure developed by the pulmonary system of the user and for releasing said inflation pressure to allow the removal of said inflatable earplugs.

FIG. 2 depicts in cutaway detail the bullet-shaped inflatable earplug 11, the plurality of integral annuli 12 and the increasing wall thickness proximate the bullet nose 15 of said earplug. Said increasing thickness 15 is provided to restrict the longitudinal expansion of the earplug to eliminate the possibility of elongation of said earplug to a point where it may come into contact with the tympanic membrane. Inflatable earplugs disclosed in the prior art or balloon-like earplugs in general, expand in all directions simultaneously and upon achieving firm contact with the auditory meatus may expand exponentially along their longitudinal axes to reach and possibly damage the tympanic membrane with potentially catastrophic result. The elongation of the earplug of the present invention is inhibited by a progressively increasing wall thickness 15 along the longitudinal axis of said earplug which restricts the inward progress of expansion as peripheral expansion occurs 20. Said increased thickness 15 in the area most proximate the tympanic membrane reduces the ability of said thickened area to vibrate in response to sound or concussive pressures thereby attenuating said pressures, preventing them from being transmitted to the tympanic membrane.

The earplugs of the present invention are inflated by mouth-blown pressure through valve means 14 which is depicted in cutaway detail in FIG. 3. Said valve means comprising an air passage 18, a check-valve or anti-reverse flow means 16 and a sealing or plug means 17, for preventing loss of inflation pressure from said earplugs during use. Said valve means 14, constructed of a soft plastic material is provided with a swing-check flap 16, which is normally closed, but opens to admit said mouth blown pressure and closes to retain said pressure within the earplug set. Upon completion of inflation of said earplugs a plug-type sealing means 17, is pressed into air passage 18, to prevent any loss of pressure which may occur as a result of leakage past check-valve 16. The application of finger-applied force to cause the plug-type sealing means 17 to seat in the air passage 18, is sufficient to collapse the retracting diaphram 19 to significantly lower the profile of said valve means as illustrated in FIG. 4 and cause additional force to be applied to seal check-valve means 16, thus further assuring the retention of pressure within the earplugs to maintain them in positive sealing engagement with the auditory meatus.

When removal of the earplugs is desired, plug means 17, is removed from air passage 18, and the valve means 14 is deformed by squeezing said valve means between the thumb and fore-finger, thus causing the check-valve 16 to leak pneumatic pressure from the flexible tube 13, and the inflated earplugs 11, causing said earplugs to deflate and diminish their contact with the auditory meatus making removal possible without damage to the sensitive tissue of the auditory canal.

FIG. 5 illustrates the manner in which the earplugs are inflated by the user by the application of mouth-blown pressure to expand the earplug inserts and (by phantom lines) the manner in which the flexible inflating tube is worn under the chin following inflation by the user, or alternately behind the neck, when inflated by a "care-giver" as may be the case with infants, the infirm or the handicapped.

FIG. 6 illustrates an alternate embodiment of the present invention wherein separate earplugs are provided for each ear. Each separate earplug comprising the same elements as heretofore described is provided with an individual inflation and deflation means identical to that previously herein disclosed. In this embodiment the external configuration of the valve means 14 is changed to accomodate a single flexible tube 13, while the internal structure of the valve means and the operation thereof remains unchanged. The placement of the flexible inflation tube 13, behind the ear, following inflation and during use, is shown by phantom lines.

FIG. 7 further illustrates the alternate embodiment of the present invention and shows to advantage, in cut-away section, the construction of valve means 14 and plug means 17.

PREFERRED EMBODIMENT OF THE INVENTION

As has been shown in the drawing figures and the succeeding description thereof, the preferred embodiment of the present invention comprises identical inserts for each ear of the user, said inserts being in the form of a hollow bullet-shaped earplugs formed of a soft, elastic closed-cell expandable material having properties to be readily cleanable and sterilizable through the use of normal sterilizing agents by immersion or by heat as in an autoclave. Said hollow, bullet-shaped inserts having a plurality of integrally formed annuli about their periphery which upon inflation of said inserts come into positive sealing engagement with the interior walls of the auditory canal to form ear plugs to exclude sound pressures, concussive shock-waves, foreign matter and fluids from the inner portions of the auditory system. Said hollow, bullet-shaped earplugs having an increasing wall thickness in the area of the bullet-nose shaped portion thereof to prevent the longitudinal expansion of said earplugs following the pneumatically induced expansion of said earplugs into contact with the walls of the auditory meatus. Said earplugs being pneumatically expandable by means of a flexible tube fixedly attached to the rear portion of the bullet-shaped insert, said tube having pneumatic integrity with said inserts. Said inserts being inter-connected by said flexible tube. Said flexible tube being of sufficient length to pass under the chin of the wearer of said earplugs and having at the mid-point thereof valve means for the admission of mouth-blown pressure and means to prevent said mouth-blown pressure from escaping said valve, said tubing and said expandable earplugs. Said valve having pressure release means whereby the user may cause said valve to release said pneumatic pressure from said earplugs and said flexible tubing to cause said earplugs to deflate and disengage the auditory meatus to allow the withdrawal of said earplugs without damage to the delicate tissue thereof.

The method and apparatus of the present invention affords simple, safe and effective means for providing improved protection of the auditory system of the user in all circumstances where such protection is required. Said means being readily cleanable and sterilizable, easily insertable and removable and capable of preventing entry into the auditory canal of damaging sound pressures and foreign matter and fluids.

While there has herein been shown and described the presently preferred form of this invention, it is to be understood that such has been done for purposes of illustration only, and that various changes may be made therein within the scope of the appended claims.

What I claim is:

1. An earplug for providing protection to a person's auditory canal comprising:
   at least one hollow expandable ear insert of a fixed shape and made of an elastomeric material and having a closed end and a side wall adapted to be inserted into a user's auditory canal, and an open end, said ear insert being sufficiently small in its unexpanded state such that the ear insert may be inserted into the user's auditory canal without abrasion to the user's auditory meatus; and
   a hollow tube having opposed open ends, an air inlet at one of said ends and an air outlet at said other end, said air outlet being attached to said open end of the ear insert, said air inlet attached to a mouthpiece adapted to be positioned at the user's mouth for allowing the user to inflate the ear insert by blowing into the air inlet.

2. The earplug of claim 1 wherein the ear insert is bullet shaped and is provided with integral annular rings adapted to firmly engage the user's auditory meatus when the ear insert is expanded.

3. The earplug of claim 2 wherein the wall thickness of the closed end of the ear insert is greater than the thickness of the side wall whereby expansion of the ear insert along its longitudinal axis is inhibited.

4. The earplug of claim 3 wherein two ear inserts are provided, one for each of the user's auditory canals, and the ear inserts are connected by a length of the hollow tube sufficient to span the distance between the user's auditory canals while passing under the user's chin, the mouthpiece being proximate the center of said length of the hollow tube such that the mouthpiece may be positioned at the user's mouth thereby allowing the user to inflate the ear inserts.

5. The earplug of claim 1 wherein the mouthpiece includes:
   an air passage having a first end extending outwardly from said mouthpiece and a second end extending inwardly toward the interior of the mouthpiece; and
   a check valve covering said second end of said air passage and being adapted to admit air into the hollow tube and the ear insert and retain the air in said hollow tube and said ear insert.

6. The earplug of claim 5 wherein said check valve comprises a flap, said flap being displaced from the second end of the air passage when the user applies mouth-blown pressure.

7. The earplug of claim 6 wherein a plug is attached adjacent the first end of said air passage to form a seal against the inadvertent escape of air from the earplug.

8. The earplug of claim 7 wherein the mouthpiece is sufficiently flexible such that
   (a) the user may pinch said mouthpiece between a thumb and a finger to allow for the escape of air from the earplug, and (b) the air passage may be collapsed toward the interior of the mouthpiece.

9. The earplug of claim 8 wherein two ear inserts are provided, one for each of the user's auditory canals, and the ear inserts are connected by a length of the hollow tube sufficient to span the distance between the user's auditory canals while passing under the user's chin, the mouthpiece being proximate the center of said length of the hollow tube such that the mouthpiece may be positioned at the user's mouth thereby allowing the user to inflate the ear inserts.

* * * * *